(12) United States Patent
Meridew et al.

(10) Patent No.: US 7,993,408 B2
(45) Date of Patent: Aug. 9, 2011

(54) ACETABULAR CUP HAVING AN ADJUSTABLE MODULAR AUGMENT

(75) Inventors: Jason D. Meridew, Syracuse, IN (US); Troy W. Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 165 days.

(21) Appl. No.: 12/029,873

(22) Filed: Feb. 12, 2008

(65) Prior Publication Data

US 2009/0204225 A1   Aug. 13, 2009

(51) Int. Cl.
*A61F 2/32* (2006.01)

(52) U.S. Cl. .................... 623/22.32; 623/22.38

(58) Field of Classification Search .... 623/22.17–22.21, 623/22.25–22.26, 22.28, 22.3, 22.35, 22.37–22.38, 623/19.11–19.14, 22.32
See application file for complete search history.

(56) References Cited

U.S. PATENT DOCUMENTS

| | | | |
|---|---|---|---|
| 4,566,138 A * | 1/1986 | Lewis et al. | 623/22.38 |
| 5,108,441 A * | 4/1992 | McDowell | 128/898 |
| 5,176,711 A | 1/1993 | Grimes | |
| 5,192,329 A | 3/1993 | Christie et al. | |
| 5,326,368 A | 7/1994 | Collazo | |
| 5,336,268 A | 8/1994 | Rispeter et al. | |
| 5,370,704 A | 12/1994 | DeCarlo, Jr. | |
| 5,549,692 A | 8/1996 | Hauser et al. | |
| 5,871,548 A | 2/1999 | Sanders et al. | |
| 5,916,268 A | 6/1999 | Schollner et al. | |
| 5,938,698 A * | 8/1999 | Sandoz et al. | 623/16.11 |
| 6,083,263 A | 7/2000 | Draenert et al. | |
| 6,162,257 A | 12/2000 | Gustilo et al. | |
| 6,454,809 B1 | 9/2002 | Tornier et al. | |
| 6,527,809 B1 | 3/2003 | Doursounian et al. | |
| 7,291,177 B2 | 11/2007 | Gibbs | |
| 2005/0021148 A1 | 1/2005 | Gibbs | |
| 2008/0009874 A1 | 1/2008 | Meridew et al. | |
| 2008/0021568 A1 | 1/2008 | Tulkis et al. | |

FOREIGN PATENT DOCUMENTS

| | | |
|---|---|---|
| EP | 0809985 | 12/1997 |
| WO | WO-02083035 | 10/2002 |

OTHER PUBLICATIONS

International Search Report mailed Jun. 25, 2009 for PCT/US2009/033668 claiming benefit of U.S. Appl. No. 12/029,873.

* cited by examiner

*Primary Examiner* — David Isabella
*Assistant Examiner* — Marcia Hoffman
(74) *Attorney, Agent, or Firm* — Harness, Dickey (57) ABSTRACT

An orthopedic prosthesis for implantation into a bone of a patient can include a shell, an augment and a securing member. The shell can be adapted to be affixed within the bone and have an outer surface adapted to receive bone ingrowth after implantation. The shell can have an inner surface adapted to engage a liner. An elongated slot can extend between the outer and inner surfaces of the shell. The augment can define a body and have a passage therethrough. The securing member can extend through the passage and the slot. The securing member can be movable between a locked position wherein the augment is precluded from relative movement with the shell and an unlocked position wherein the securing member is adapted to slidably traverse along the slot to locate the augment at a plurality of positions relative to the shell.

25 Claims, 8 Drawing Sheets

ACETABULAR CUP HAVING AN ADJUSTABLE MODULAR AUGMENT

FIELD

The present disclosure relates to acetabular cups and more particularly to an acetabular cup having an adjustably secured augment.

INTRODUCTION

A natural hip joint may undergo degenerative changes due to a variety of etiologies. When such degenerative changes become so far advanced and irreversible, it may ultimately become necessary to replace a natural hip joint with a prosthetic hip. If the acetabulum needs repair, all remnants of articular cartilage may be removed from the acetabulum and an acetabular prosthesis which will accommodate the head or ball of the hip prosthesis may be affixed to the acetabulum.

In some instances however, it may also be necessary to remove a defect located adjacent the acetabulum. Such defects may be located in various areas adjacent the acetabulum depending on a given patient. In one example, an augment may be implanted adjacent an acetabular cup to account for the area of the removed defect. In general, traditional acetabular cups and augments are configured to be implanted in a certain orientation relative to the acetabulum. Therefore, such acetabular cups and augments provide limited versatility requiring a high inventory of augments and acetabular cups to meet patient needs.

SUMMARY

An orthopedic prosthesis for implantation into a bone of a patient can include a shell, an augment and a securing member. The shell can be adapted to be affixed within the bone and have an outer surface adapted to receive bone ingrowth after implantation. The shell can have an inner surface adapted to engage a liner. An elongated slot can extend between the outer and inner surfaces of the shell. The augment can define a body and have a passage therethrough. The securing member can extend through the passage and the slot. The securing member can be movable between a locked position wherein the augment is precluded from relative movement with the shell and an unlocked position wherein the securing member is adapted to slidably traverse along the slot to locate the augment at a plurality of positions relative to the shell.

According to additional features, a transition between the slot and the inner surface of the shell can be defined by a channel. The securing member can define a shell end and an augment end. The shell end can be nested in the inner surface of the shell in the locked position. The augment end can be nested into the body to a location inboard of an outer augment surface.

In one example, the securing member can collectively define a fastener and a nut. The fastener can define a threaded shaft and a head. The threaded shaft can threadably engage a bore defined through the nut in the locked position. The head can be adapted to nest in one of the shell and the augment in the locked position. The nut can be adapted to nest in the other of the shell and the augment in the locked position. The nut can define a concave proximal profile that substantially conforms to the inner surface of the shell. The head of the fastener can be adapted to nest on an annular ridge defined in the augment body in the locked position.

The augment can define a shell facing surface having a plurality of protrusions formed thereon. The shell facing surface can be offset from the outer surface of the shell in the locked position by the protrusions.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of various embodiment(s) is merely exemplary in nature and is in no way intended to limit the application or uses.

Figure 1:
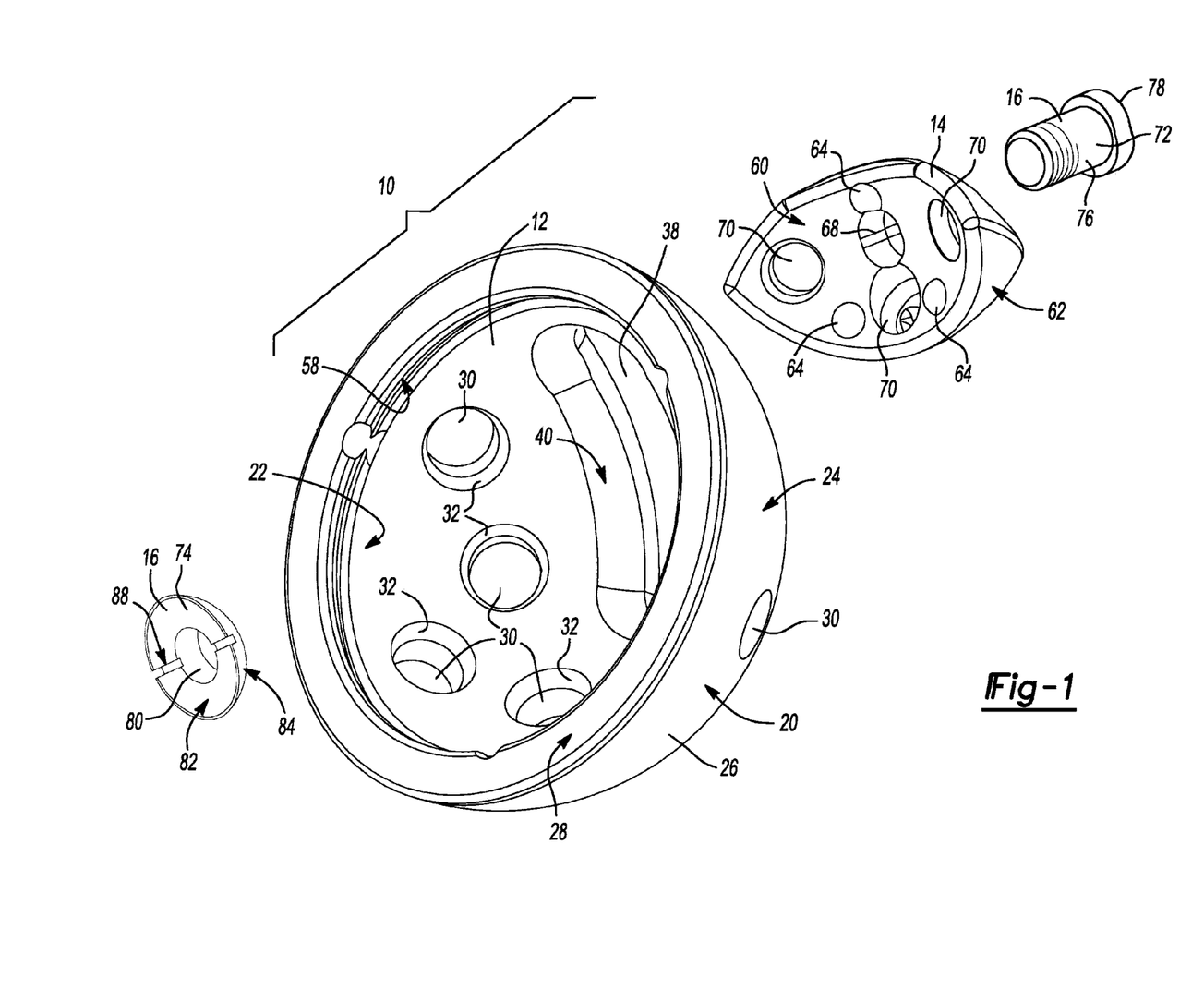
FIG. 1 is an exploded perspective view of an orthopedic prosthesis including a shell, an augment and a securing member according to one example of the present teachings.
Figure 2:
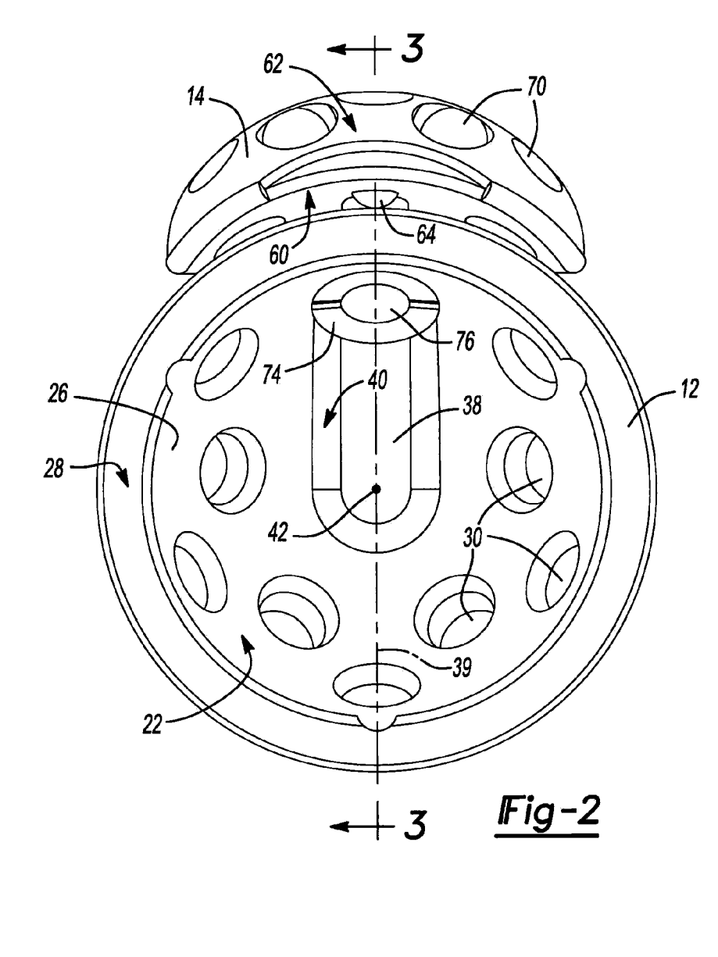
FIG. 2 is a top view of the orthopedic prosthesis of FIG. 1 shown in an assembled position.

With initial reference to FIGS. 1 and 2, an orthopedic prosthesis for implantation into a bone of a patient is shown and generally identified at reference numeral 10. While the following discussion is directed toward implantation of the orthopedic prosthesis 10 into an acetabulum of a hip, it is appreciated that the following teachings may be applicable for other prosthesis for implantation to other areas such as implantation into a glenoid for a shoulder.

The orthopedic prosthesis 10 can generally include an acetabular cup 12, an augment 14 and a securing member 16. The acetabular cup 12 can generally define a shell 20 having an inner surface 22 and an outer surface 24. The shell 20 can be collectively defined by a body portion 26 and an upper rim 28. A plurality of holes 30 may be defined through the shell 20. Each of the plurality of holes 30 can include an arcuate entrance surface 32 formed at the inner surface 22. The arcuate entrance surface 32 can be adapted to nestingly receive a head of a fastener such as a bone screw (not shown). The configuration and orientation of the holes 30 are merely exemplary. An elongated slot 38 can be formed in the acetabular cup 12 and extend between the inner and outer surfaces 22 and 24, respectively. The elongated slot 38 can extend along a radial axis 39 (FIG. 3) of the shell 20. The elongated slot 38 can be bound by a channel 40. The channel 40 can be defined at a transition between the elongated slot 38 and the inner surface 22 of the acetabular cup 12. The channel 40 can have a generally concave surface. In one example, the elongated slot 38 can be generally perpendicular to the rim 28 or radially extending from the dome or apex of the shell 20. The elongated slot 38 can extend between a first terminal end positioned at an apex 42 of the shell 20 and a second terminal end positioned between the apex 42 and the upper rim 28 of the shell 20.

Figure 3:
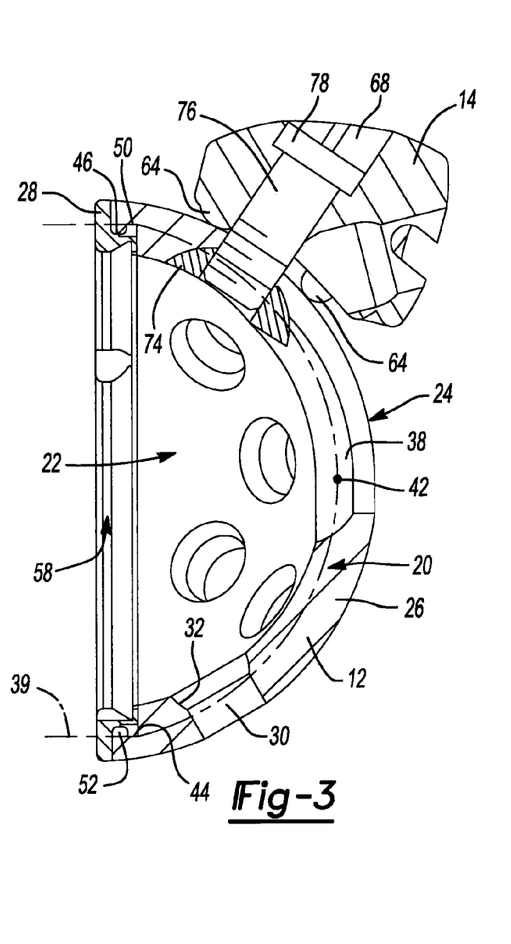
FIG. 3 is a sectional view of the orthopedic prosthesis taken along line 3-3 of FIG. 2.

In one example, the upper rim 28 can be joined to the body portion 26 during a molding process. As best shown in FIG. 3, a first annular pocket 44 can be defined around an inner radius of the body portion 26. Similarly, a second annular pocket 46 can be defined around an outer radius of the upper rim 28. A first collar 50 formed on the upper rim 28 can nest in the first annular pocket 44 of the body portion 26. A second collar 52 formed on the body portion 26 can nest in the second annular pocket 46 of the upper rim 28. The respective pockets 44 and 46 and collars 50 and 52 can provide an overhanging interlock between the body portion 26 and the upper rim 28 for increased structural integrity of the shell 20. A liner 56 (FIGS. 5 and 6) can be captured within the shell 20 by an annular ring (not shown) received within an annular pocket 58 (FIG. 1). In one example, the body 26 can be formed entirely or partially of porous metal (such as porous coated). In one example, the porous metal may comprise stainless steel, titanium, titanium alloys, cobalt-chromium alloys and other materials that are suited for use in a biocompatible environment. The outer surface 24 may be adapted to receive bone ingrowth after implantation. The upper rim 28 can be formed of non-porous metal. The non-porous metal can comprise stainless steel, titanium, titanium alloys, cobalt-chromium alloys and other materials that are suited for use in a biocompatible environment. A series of cups 12 having various sizes and/or porosity may be provided.

The augment 14 will now be described in detail. The augment 14 can generally define a cup-facing surface 60 (FIG. 1) and an outer bone engaging surface 62. The cup-facing surface 60 can be generally concave and include a plurality of protrusions 64 formed thereon. The protrusions 64 are shown generally in the form of semi-hemispherical knobs. Other geometries and configurations are contemplated. In an implanted position, the protrusions 64 can engage the outer surface 24 of the cup 12 thereby offsetting the cup-facing surface 60 of the augment 14 from the outer surface 24 of the cup 12 (FIG. 3). A passage 68 can be formed through the augment 14 for receiving the securing member 16. A plurality of bores 70 can be defined through the augment 14. In one example, fasteners such as bone screws (not shown) may be inserted interoperatively through the plurality of bores 70.

In one example, the augment 14 may be formed of porous metal such as by one of the materials disclosed herein. A series of augments having various sizes and/or porosity may be provided. In general, the augment 14 may be used to fill an area adjacent the acetabular cup 12 such as where a bone defect was removed.

The securing member 16 will now be described in detail. The securing member 16 can collectively define a fastener 72 and a nut 74. The fastener 72 can define a threaded shaft 76 and a head 78. The nut 74 can define a threaded bore 80, a proximal surface 82, and a distal surface 84. The proximal surface 82 can be generally concave to substantially conform to the inner surface 22 of the shell 20. The concave proximal surface 82 can define a slot 88. The slot 88 can facilitate gripping of the nut 74 such as to impose rotational motion by a tool (not shown). The distal surface 84 can be generally convex to substantially conform to the profile of the annular channel 44 for slidable communication therealong as will be described.

Figure 4:
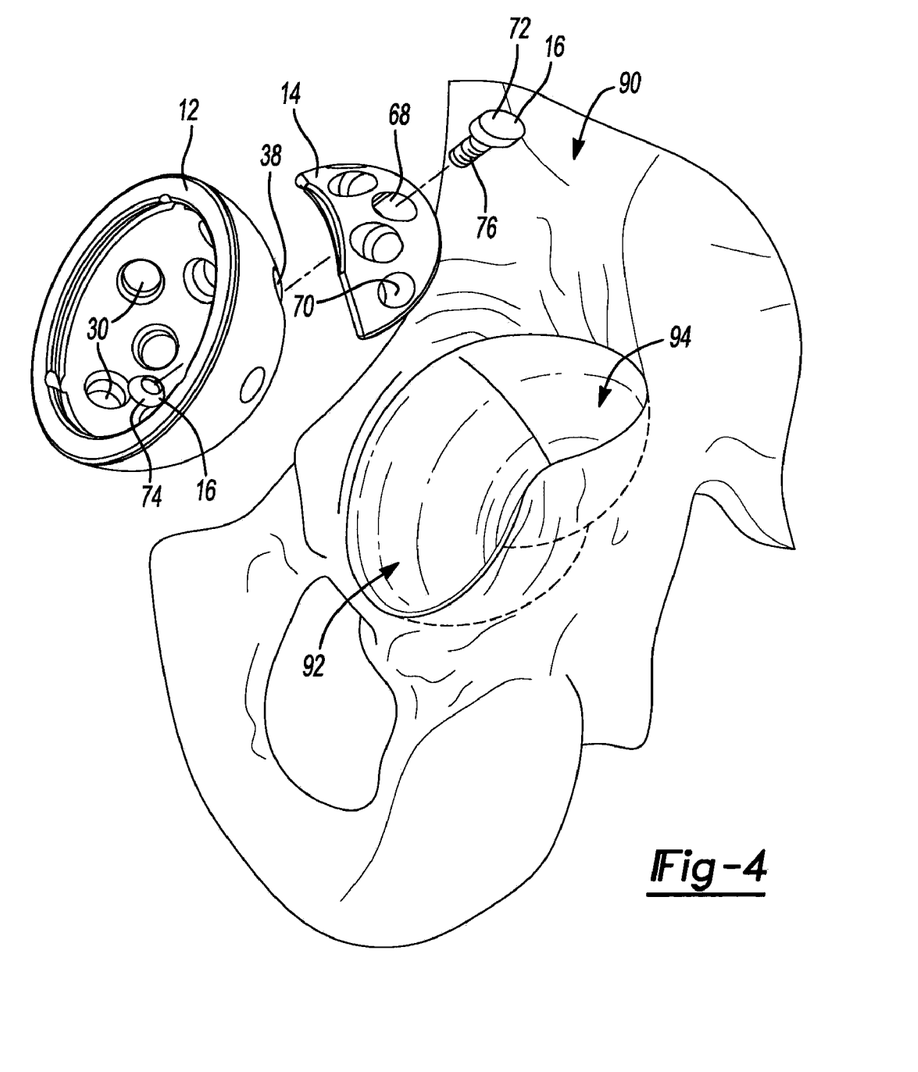
FIG. 4 is an exploded perspective view of the orthopedic prosthesis shown prior to implantation into an acetabular socket.
Figure 5:
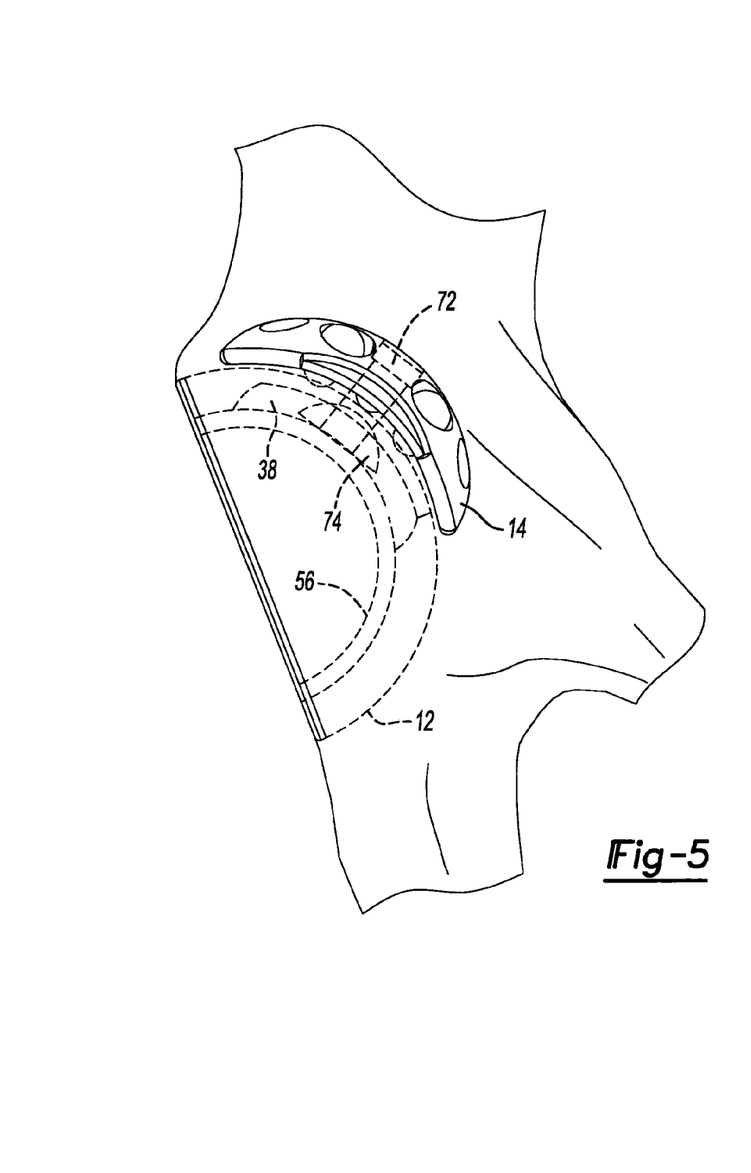
FIG. 5 is a side view of the orthopedic prosthesis of FIG. 4 shown with the augment implanted into the acetabular socket in a first location.
Figure 6:
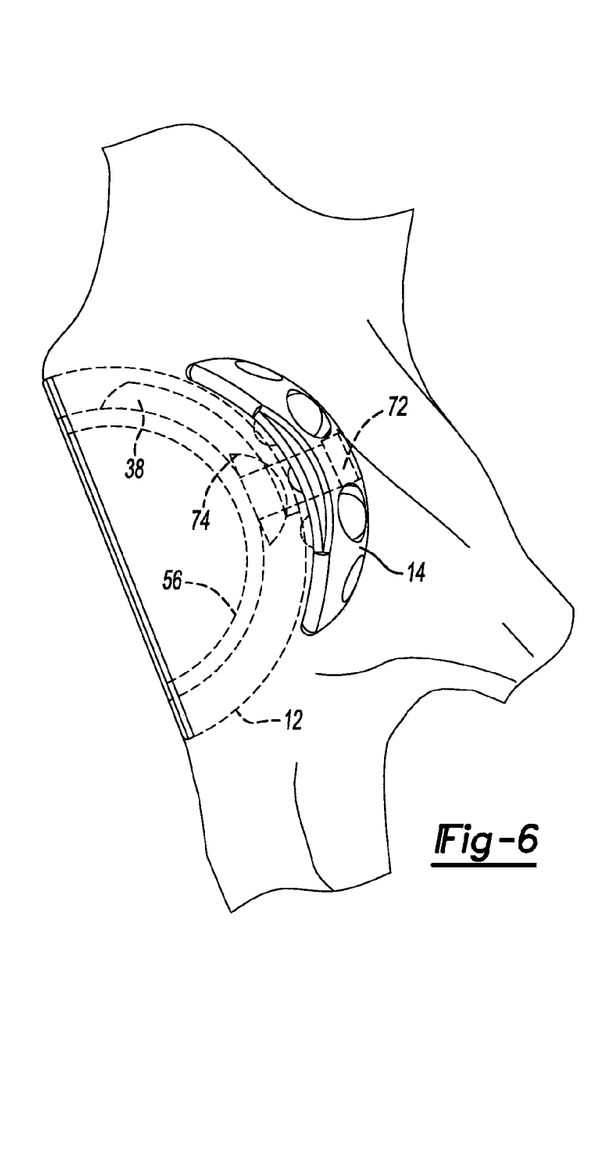
FIG. 6 is a side view of the orthopedic prosthesis of FIG. 4 shown with the augment implanted into the acetabular socket in a second location.

With particular reference now to FIGS. 4-6, preparation of an acetabulum 90 and implantation of the orthopedic prosthesis 10 will be described. Initially, a driver (not shown) may be operably coupled to impart rotational force through a reamer drive shaft to a cutting head. One exemplary method for preparing the acetabulum 90 may be found in co-pending application, U.S. Ser. No. 11/453,312 filed Jun. 14, 2006, entitled "Method and Apparatus for Reaming an Acetabulum" also assigned to Biomet, Inc., of Warsaw Ind., which is incorporated herein by reference. The acetabulum 90 may be generally hemispherically reamed until concentric removal of all acetabular cartilage and/or bone cement is achieved. The reamed area can be referred to as an acetabular cup socket 92. Once the acetabulum 90 has been appropriately reamed, acetabular trial gauges (not shown), which are well known in the art, may be used to determine and confirm the diameter of the acetabular cup 12 to be used. At this point, a surgeon may access the defect to be reamed and identify which reamer tool to select for achieving the proper reaming area. The defect is then reamed. The resultant reamed area outside of the acetabular cup socket 92 can be generally referred to as an augment socket 94.

Once the acetabulum 90 has been sufficiently prepared, a surgeon can select an appropriately sized acetabular cup 12 and augment 14 for the acetabular cup socket 92 and augment socket 94, respectively.

Next, the acetabular cup 12, augment 14 and securing member 16 can be generally placed proximate to the acetabulum 90. In one example, the shaft 76 of the fastener 72 can be inserted through the passage 68 of the augment 14 just prior to positioning the augment 14 into the augment socket 94. In one method, the shaft 76 of the fastener 72 can be located through the slot 38 of the cup 12 prior to positioning of the augment 14 into the augment socket 94. It is contemplated that the shaft 76 can alternatively be located through the slot 38 during or subsequent to positioning of the augment 14 into the augment socket 94. Next, the surgeon can slide the shaft 76 of the fastener 72 along the slot 38 to orient the augment 14 in a desired location relative to the cup 12. This adjustability can be particularly useful to a surgeon in that the location of the augment 14 relative to the cup 12 can be adjusted to substantially conform with a location of the augment socket 94 relative to the acetabular cup socket 92. As mentioned above, a plurality of different sized cups 12 and augments 14 can be provided to further accommodate the needs of a particular patient.

As shown in FIGS. 5 and 6, the shaft 76 can be located in a first position (FIG. 5) and a second position (FIG. 6) to locate the augment 14 at distinct locations along the outer surface 24 of the cup 12. It is appreciated that the shaft 76 can slidably translate along the entire slot 38 offering a plurality of possible fixed locations the augment 14 can occupy relative to the cup 12. Once a desired location has been attained, the nut 74 can be threadably tightened onto the shaft 76 of the fastener 72 to lock the augment 14 in a locked or fixed location relative to the cup 12.

It is appreciated that the acetabular cup 12 may be secured to the acetabular cup socket 92 by any suitable methods such as bone screws (not shown) driven through the holes 30 and/or bone cement. Likewise, bone screws (not shown) may additionally or alternatively be located through the bores 70 of the augment 14 to secure the augment 14 into the augment socket 94. The sequence of securing the augment 14 relative to the cup 12, the cup 12 relative to the acetabular cup socket 92, and the augment 14 relative to the augment socket 94 can be determined by the surgeon. In one example, the acetabular cup 12 and the augment 14 can be loosely coupled together with the securing member 16. The loosely assembled acetabular cup 12 and augment 14 can then be located into the acetabular cup socket 92 and the augment socket 94, respectively. The surgeon can then move the augment 14 and/or the acetabular cup 12 by moving the shaft 76 of the fastener 72 between various positions along the slot 38 to attain a desired position as described above. Once a desired position has been attained, the nut 74 can be tightened to lock the assembly as described above. At this point, the acetabular cup 12 and the augment 14 can be fixed to the respective acetabular cup socket 92 and the augment socket 94, respectively. In other examples, one of the acetabular cup 12 and the augment 14 can be secured into the acetabular cup socket 92 and the augment socket 94 prior to locking the relative position of the acetabular cup 12 and the augment 14 with the securing member 16.

Figure 7:
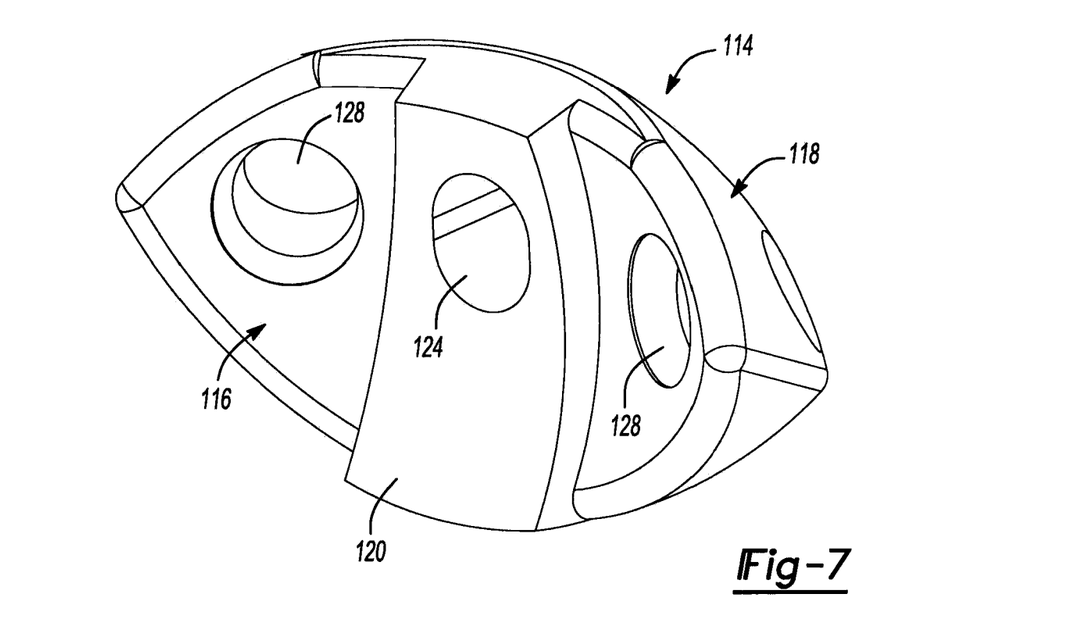
FIG. 7 is a perspective view of an augment according to additional features.

With reference to FIG. 7, an augment 114 constructed in accordance to additional features is shown. The augment 114 can generally include a concave cup-facing surface 116 and an outer bone engaging surface 118. The cup-facing surface 116 can include a central keel portion 120. In an implanted position, the central keel portion 120 can engage the outer surface 24 of the cup 12 thereby offsetting the remainder of the cup-facing surface 116 of the augment 114 from the outer surface 24 of the cup 12. A passage 124 can be formed through the augment 114 for receiving the securing member 16. A plurality of bores 128 can be defined through the augment 114. In one example, fasteners such as bone screws (not shown) may be inserted intraoperatively through at least one of the plurality of bores 128.

Figure 8:
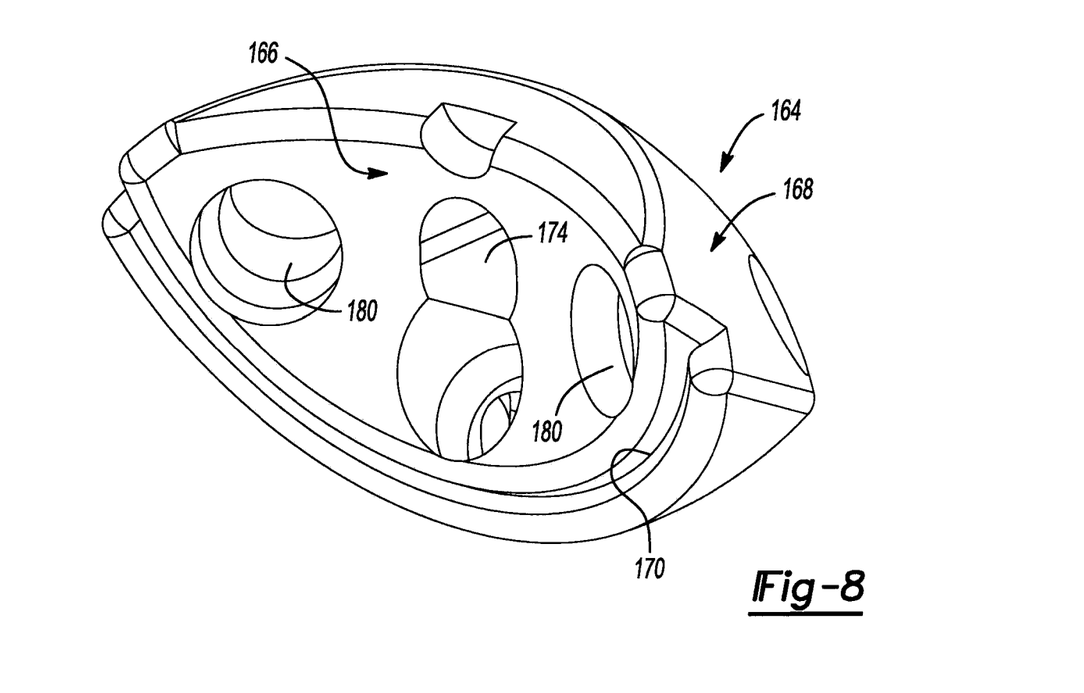
FIG. 8 is a perspective view of another augment according to additional features.
Figure 9:
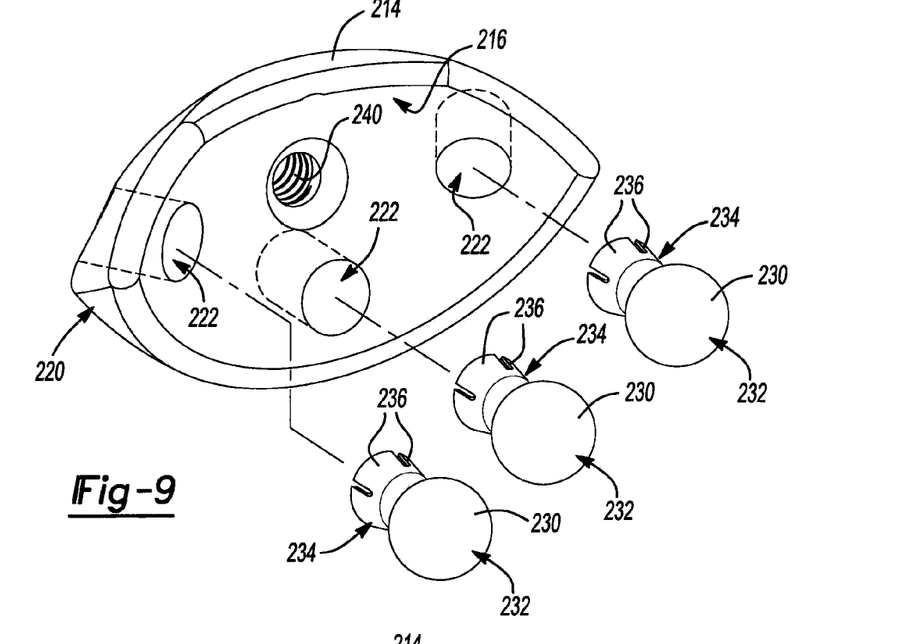
FIG. 9 is an exploded view of another augment according to additional features and having selectively attachable spacer members.
Figure 10:
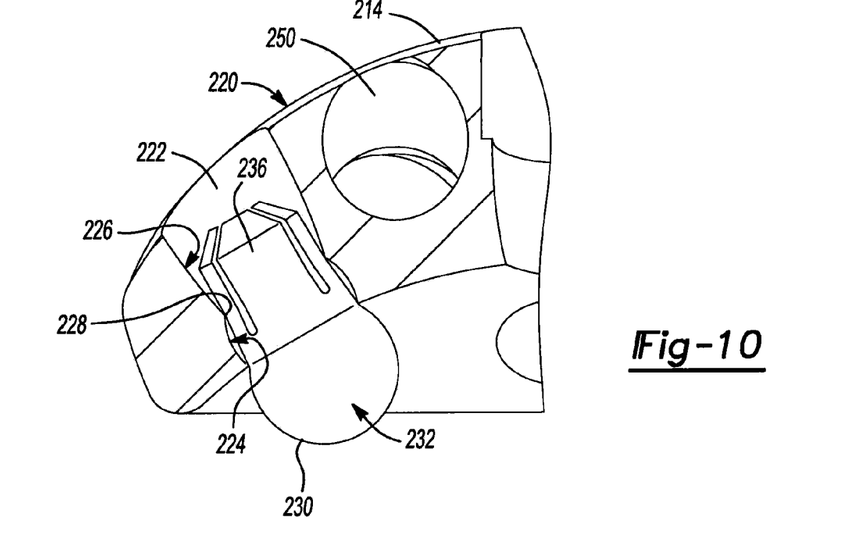
FIG. 10 is a sectional view of the augment of FIG. 9 shown with a spacer member in an installed position.
Figure 11:
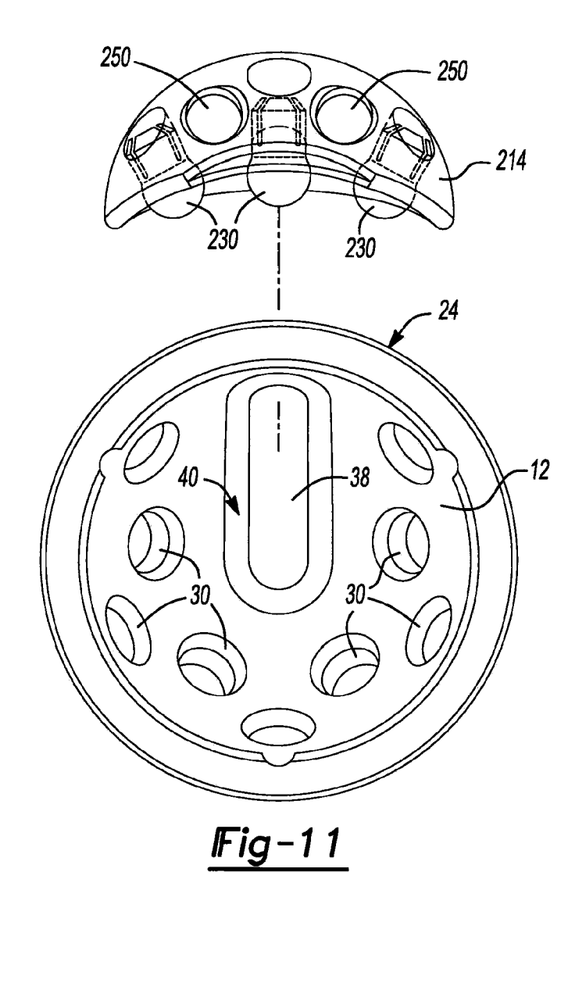
FIG. 11 is an exploded view of an orthopedic prosthesis and the augment shown in FIG. 9 shown with a plurality of spacers in an installed position.

With reference to FIG. 8, an augment 164 constructed in accordance to additional features is shown. The augment 164 can generally include a concave cup-facing surface 166 and an outer bone engaging surface 168. The cup-facing surface 166 can include a stepped arcuate edge portion 170. In an implanted position, the stepped arcuate edge portion 170 can be offset away from engagement with the outer surface 24 of the cup 12. A passage 174 can be formed through the augment 164 for receiving the securing member 16. A plurality of bores 180 can be defined through the augment 164. In one example, fasteners such as bone screws (not shown) may be inserted intraoperatively through at least one of the plurality of bores 180.

Turning now to FIGS. 9-14, an augment 214 according to additional features will be described in detail. The augment 214 can generally define a cup-facing surface 216 (FIG. 9) and an outer bone engaging surface 220. A plurality of receptacles 222 can be defined in the cup-facing surface 216 of the augment 214. In one example, the receptacles 222 can define an annular ramped portion 224 (FIG. 10) and an annular flared portion 226. The annular ramped portion 224 can transition to the annular flared portion 226 at a neck 228. While the receptacles 222 are shown extending completely through the augment 214, it is appreciated that they may alternatively form blind bores that do not extend completely through the augment 214.

The cup-facing surface 216 can be generally concave and include a plurality of spacers 230 removably coupled thereto. Each of the spacers 230 can generally include a body portion 232 and a stem portion 234. The stem portion 234 can have a plurality of annular feet 236. The annular feet 236 can initially deflect inward during insertion into the receptacles 222 defined in the augment 214 and rebound to a relaxed state (FIG. 10) to provide an outward bias or retaining force onto the receptacles 222 once inserted. The stems 234 of the spacers 230 can be inserted into the receptacles 222 in any manner such as a snap-fit, press-fit, tolerance-fit, or clearance-fit. In other examples, the spacers 230 can be additionally or alternatively coupled to the augment 214 with a flowable adhesive such as bone cement.

Figure 12:
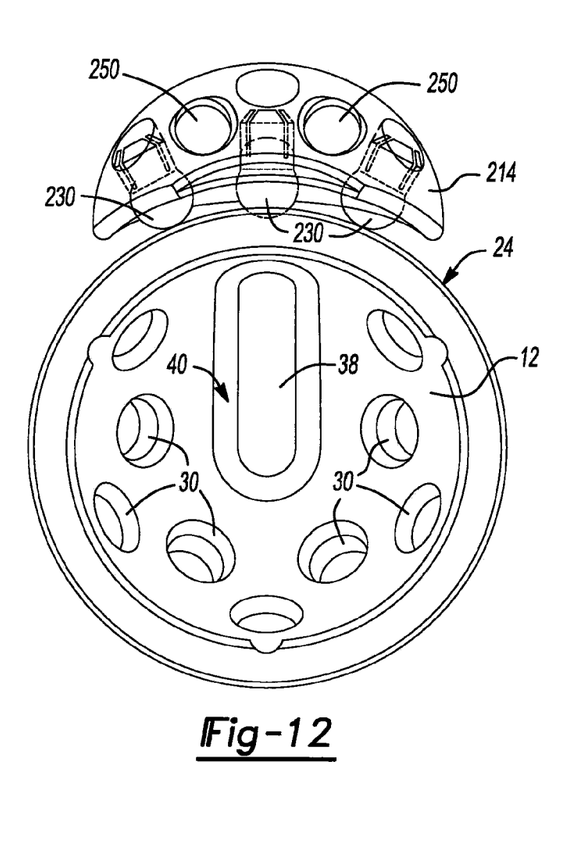
FIG. 12 is a top view of the orthopedic prosthesis of FIG. 11 shown in an assembled position.

The body portions 232 of the spacers 230 are shown generally in the form of spherical knobs. Other geometries and configurations are contemplated. In an implanted position, the body portions 232 of the spacers 230 can engage the outer surface 24 of the cup 12 (and act as protrusions extending from the augment 214) thereby offsetting the cup-facing surface 216 of the augment 214 from the outer surface 24 of the cup 12 (FIG. 12). In one example, such a configuration may be useful in providing a desired offset between the augment 214 and the cup 12 to satisfy the required spacing between a given augment socket 94 (FIG. 4) and acetabular cup socket 92. A passage 240 (FIG. 10) can be formed through the augment 214 for receiving the securing member 16. While not shown in FIG. 9 for clarity, a plurality of bores 250 (FIGS. 10-14) can be defined through the augment 214 such as described above with respect to augment 14. In one example, fasteners such as bone screws (not shown) may be inserted interoperatively through the plurality of bores 250.

Figures 13, 14:
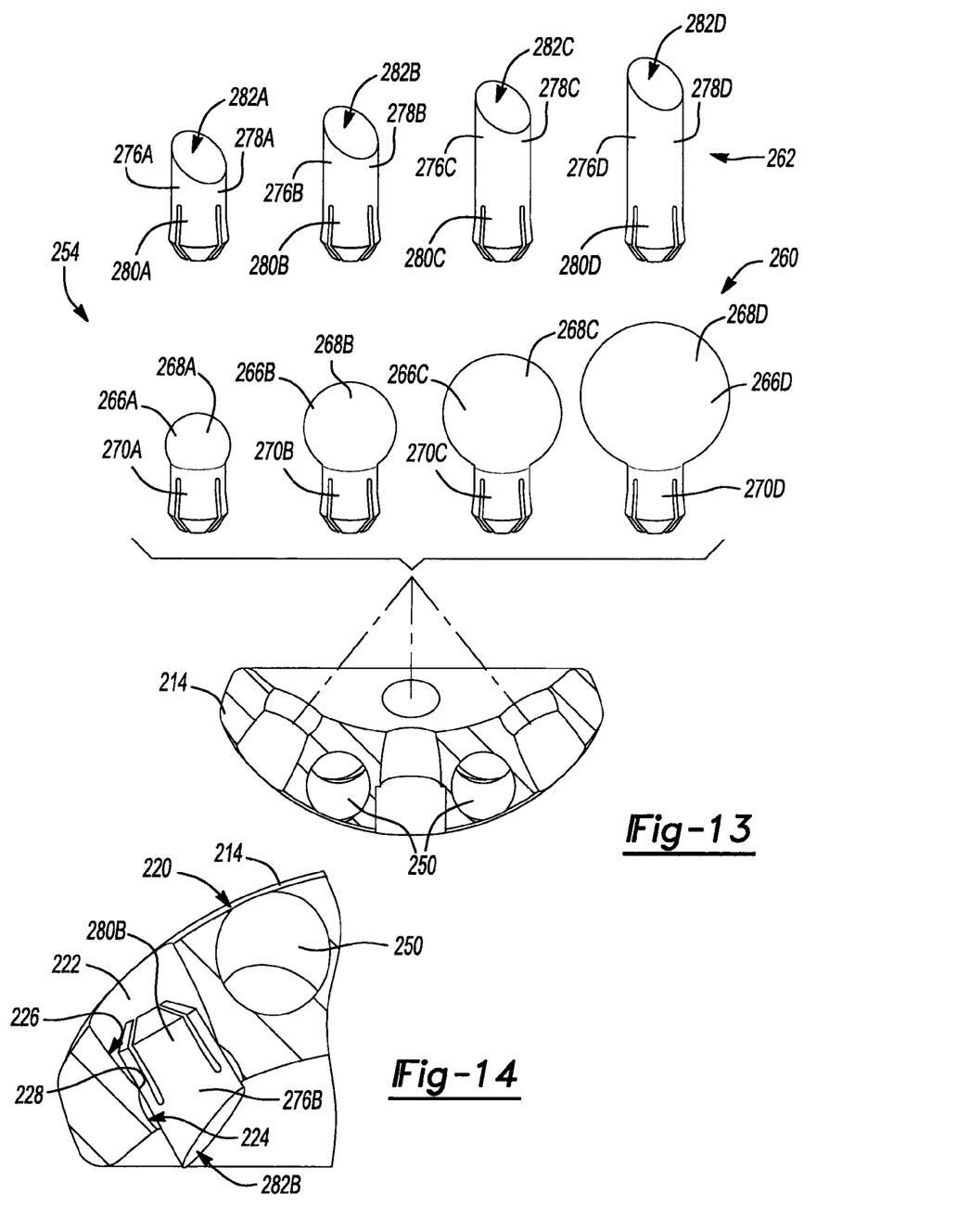
FIG. 13 is an exploded view of an augment shown with a plurality of spacers.
FIG. 14 is a sectional view of the augment of FIG. 13 shown with one of the augments in FIG. 13 in an installed position.

With reference now to FIG. 13, a kit 254 including an augment 214, a first plurality of spacers generally identified at 260 and a second plurality of spacers generally identified at 262 is shown. The first plurality of spacers 260 can generally take the form of the spacers 230 but have body portions defining various sizes. The first plurality of spacers 260 can include spacers 266A, 266B, 266C, and 266D. The first plurality of spacers 266A-266D can define body portions 268A-268D and stem portions 270A-270D, respectively. In general, the second plurality of spacers 262 can include a stem portion equivalent to the stems 234, but define a body portion comprising a generally longitudinal section and having an angled distal end. The second plurality of spacers 262 can include spacers 276A, 276B, 276C, and 276D. The second plurality of spacers 276A-276D can define body portions 278A-278D and stem portions 280A-280D, respectively. The stem portions 280A-280D can define angled distal ends 282A-282D. In one example, a spacer of the second plurality of spacers 262 can be rotated about its longitudinal axis to position the angled distal end (282A-282D) at a desired orientation.

As shown, each of the body portions 276A-276D (longitudinal sections) can define a different length. The second plurality of spacers 262 can couple to the receptacle 222 as described above. As can be appreciated, a surgeon can select any combination of the first and second plurality of spacers 260 and 262 to define a desired offset between the cup 12 and the augment 14 depending on a given patient. It is appreciated that in some examples, it may be desirable to incorporate a combination of spacers onto a given augment wherein each or some of the spacers have a body portion that defines a distinct size/shape to achieve various offsets.

While the disclosure has been described in the specification and illustrated in the drawings with reference to various embodiments, it will be understood by those skilled in the art that various changes may be made and equivalents may be substituted for elements thereof without departing from the scope of the disclosure as defined in the claims. For example, while the preceding discussion has been directed toward a slot 38 having a generally uniform and linear pattern, the slot 38 may define other patterns for locating the augment 14 at various positions relative to the acetabular cup 12. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the disclosure without departing from the essential scope thereof. Therefore, it is intended that the disclosure not be limited to the particular embodiment illustrated by the drawings and described in the specification as the best mode presently contemplated for carrying out this disclosure, but that the disclosure will include any embodiments falling within the foregoing description and the appended claims.

What is claimed is:

1. An orthopedic prosthesis for implantation into a bone of a patient, said orthopedic prosthesis comprising:
   a shell adapted to be affixed within the bone, said shell having an outer bone engaging surface, an inner surface, and an elongated continuously open slot that extends along a radial axis of said shell between a first terminal end positioned near an apex of said shell and a second terminal end positioned between said apex and an upper rim of said shell, said continuously open slot extending through said outer and inner surfaces;
   an augment having a body that includes a shell facing surface having a plurality of protrusions integrally formed thereon, said plurality of protrusions collectively defining an outer boundary configured to engage the outer surface of the shell thereby offsetting the shell facing surface of the augment from the outer surface of the shell, said body defining a passage through said augment at a location inward of said outer boundary; and
   a securing member extending through said passage and said continuously open slot, wherein said securing member is movable between a locked position wherein said augment is precluded from relative movement with said shell and an unlocked position wherein said securing member is adapted to move between a first fixed position on said continuously open slot and a second fixed position on said continuously open slot to locate said augment at said first and second fixed positions against said outer bone engaging surface and along said radial axis, wherein said shell facing surface is offset from said outer bone engaging surface in said locked position by said plurality of protrusions.

2. The orthopedic prosthesis of claim 1 wherein a transition between said continuously open slot and said inner surface of said shell is defined by a channel.

3. The orthopedic prosthesis of claim 2 wherein said securing member defines a shell end and an augment end, wherein said shell end is nested in said inner surface in said locked position.

4. The orthopedic prosthesis of claim 3 wherein said shell end of said securing member is nested in said channel in said locked position.

5. The orthopedic prosthesis of claim 2 wherein said securing member defines a shell end and an augment end, wherein said augment end is nested into said body to a location inboard of an outer augment surface.

6. The orthopedic prosthesis of claim 2 wherein said securing member collectively defines a fastener and a nut.

7. The orthopedic prosthesis of claim 6 wherein said fastener includes a threaded shaft defining a longitudinal axis and a head, said threaded shaft threadably engaging a bore defined through said nut in said locked position, wherein a portion of said longitudinal axis that extends through said augment is located within said outer boundary.

8. The orthopedic prosthesis of claim 7 wherein said head nests in one of said shell and said augment in said locked position and said nut nests in the other of said shell and said augment in said locked position.

9. The orthopedic prosthesis of claim 8 wherein said nut defines a concave proximal profile that substantially conforms to said inner surface of said shell.

10. The orthopedic prosthesis of claim 7 wherein said head is adapted to nest on an annular ridge defined in said augment body in said locked position.

11. The orthopedic prosthesis of claim 1 wherein said shell comprises an acetabular shell.

12. The orthopedic prosthesis of claim 1 wherein said securing member is adapted to slidably traverse along said elongated continuously open slot to locate said augment at a plurality of positions relative to said shell.

13. The orthopedic prosthesis of claim 1 wherein said elongated continuously open slot extends along said shell in a direction generally transverse to an upper rim of said shell.

14. The orthopedic prosthesis of claim 1 wherein said augment defines a plurality of bores that extend entirely through said body from said shell facing surface to an outer surface.

15. An orthopedic prosthesis for implantation into a bone of a patient, said orthopedic prosthesis comprising:
   a shell adapted to be affixed within the bone, said shell having an outer bone engaging surface, an inner surface and an elongated continuously open slot formed through said inner and outer surfaces and extending along a radial axis of said shell;
   an augment having a body that includes a shell facing surface having a plurality of protrusions integrally formed thereon and configured to engage the outer surface of the shell thereby offsetting the shell facing surface of the augment from the outer surface of the shell, wherein straight lines drawn between outermost protrusions of said plurality of protrusions collectively define an outer perimeter, said body defining a passage through said augment at a location inward of said outer perimeter; and
   a securing member including a shaft having a longitudinal axis, said shaft extending into and out of said continuously open slot and into said augment at a location such that said shaft, at said longitudinal axis, extends inward of said outer perimeter, wherein said securing member is movable between a locked position wherein said augment is precluded from relative movement with said shell and an unlocked position wherein said securing member is adapted to locate at various locations along said continuously open slot to locate said augment at a plurality of distinct, fixed positions relative to said shell, wherein said shell facing surface is offset from said outer bone engaging surface in said locked position by said plurality of protrusions.

16. The orthopedic prosthesis of claim 15 wherein a transition between said continuously open slot and said inner surface of said shell is defined by a channel and wherein said securing member defines a shell end and an augment end, wherein said shell end is nested in said inner surface in said locked position.

17. The orthopedic prosthesis of claim 16 wherein said shell end of said securing member is nested in said channel in said locked position.

18. The orthopedic prosthesis of claim 15 wherein said securing member is adapted to slidably traverse along said continuously open slot to locate said augment at a plurality of positions relative to said shell.

19. The orthopedic prosthesis of claim 15 wherein said continuously open slot extends between a first terminal end positioned near an apex of said shell and a second terminal end positioned between said apex and an upper rim of said shell.

20. The orthopedic prosthesis of claim 19, further comprising a liner that is captured only at a single fixed location relative to said radial axis of said shell against said inner surface of said shell.

21. The orthopedic prosthesis of claim 15 wherein said augment defines a plurality of bores that extend entirely through said body from said shell facing surface to an outer surface.

22. An orthopedic prosthesis for implantation into a bone of a patient, said orthopedic prosthesis comprising:
a shell adapted to be affixed within the bone, said shell having an outer bone engaging surface, an inner surface, and a first elongated engagement portion formed through said inner and outer surfaces and along a radial axis of said shell;
a liner captured only at a single fixed location relative to said radial axis of said shell and against said inner surface of said shell;
an augment having a body that has a second engagement portion formed thereon, said body further including a shell facing surface having a plurality of protrusions integrally formed thereon, said plurality of protrusions providing engaging points that collectively define an outer boundary and that engage said outer bone engaging surface in a plurality of positions and thereby offsetting the shell facing surface of the augment from the outer surface of the shell throughout engagement; and
a securing member extending between said first and second engagement portions at a location such that said securing member extends through said augment and inward of said outer boundary, said securing member selectively coupling said augment to said shell, wherein said securing member is operable to move with said augment between a plurality of discrete locked positions wherein said augment is precluded from relative movement with said shell and an unlocked position wherein said augment is adapted to slidably communicate along said radial axis of said shell and along said outer surface of said shell to locate said augment at the plurality of positions relative to said shell, wherein said shell facing surface is offset from said outer bone engaging surface in each of said plurality of discrete locked positions by said plurality of protrusions.

23. The orthopedic prosthesis of claim 22 wherein said first engagement portion defines a continuously open slot that passes through the inner and outer surfaces and extends between a first terminal end positioned near an apex of said shell and a second terminal end positioned between said apex and a rim of said shell and wherein said securing member defines a fastener and nut, wherein said fastener is adapted to communicate along said continuously open slot to locate said augment at said plurality of positions relative to said shell.

24. The orthopedic prosthesis of claim 22 wherein said augment defines a shell facing surface that slidably and freely communicates along said outer surface of said shell while in said unlocked position.

25. The orthopedic prosthesis of claim 22 wherein said augment defines a plurality of bores that extend entirely through said body from said shell facing surface to an outer surface.

* * * * *